United States Patent [19]

Tennyson

[11] Patent Number: 5,104,900

[45] Date of Patent: Apr. 14, 1992

[54] NAPHTHALENE BASED SNAKE REPELLANT

[76] Inventor: James B. Tennyson, Rte. 1, Townhouse Apt. C-7, Camilla, Ga. 31730

[21] Appl. No.: 486,375

[22] Filed: Feb. 28, 1990

[51] Int. Cl.$^5$ .................. A01N 27/00; A01N 29/04; A01N 59/02

[52] U.S. Cl. .................. 514/765; 514/751; 514/756; 514/766; 514/918; 514/957; 424/704; 424/713

[58] Field of Search ............ 514/918, 789, 957, 751, 514/752, 753, 754, 756, 765, 766; 424/405, 704, 489, 713

[56] References Cited

U.S. PATENT DOCUMENTS

| | | | |
|---|---|---|---|
| 1,097,406 | 5/1914 | Erlenbach | 514/751 |
| 2,017,506 | 10/1935 | Mills | 514/751 |
| 2,306,434 | 12/1942 | Goodhur et al. | 43/129 |
| 2,558,942 | 7/1951 | Eagleson | 424/602 |
| 2,627,488 | 2/1953 | Zakheim | 514/751 |
| 3,342,577 | 9/1967 | Blouin et al. | 71/3 |

FOREIGN PATENT DOCUMENTS

| | | | |
|---|---|---|---|
| 7103080 | 12/1968 | Japan | 514/753 |
| 0261055 | 11/1926 | United Kingdom | 514/753 |
| 0437151 | 10/1935 | United Kingdom | 514/753 |
| 0652245 | 10/1951 | United Kingdom | 514/753 |

OTHER PUBLICATIONS

The Merck Index-Tenth Edition-p. 914 (#6220).

*Primary Examiner*—Frederick E. Waddell
*Assistant Examiner*—T. J. Criares
*Attorney, Agent, or Firm*—Sherman and Shalloway

[57] ABSTRACT

A new use for naphthalene comprising a snake repellant in the form of granules comprising 8% naphthalene, 32% sulfur and 60% montmorillonite. The compound is spread in a strip across an area where snakes are to be repelled and is effective against venomous and non-venomous varieties.

8 Claims, No Drawings

NAPHTHALENE BASED SNAKE REPELLANT

BACKGROUND OF THE INVENTION

Field of the Invention

The fear of snakes, both reasonable and unreasonable, is one of the stronger phobias present in man. The fear, dread and disgust engendered by these reptiles has been reinforced by various religious teachings and popular fictions to the extent that the common reaction upon encountering a snake is to kill it. This is particularly the case with venomous snakes because of the significant danger presented by these creatures to humans and pets. In addition, the bite of a non-venomous snake, although not as dangerous as that of the venomous varieties, can be extremely painful and has the potential to be infectious.

However, snakes do serve a useful purpose in the control of other pests, notably rats, mice and the like, and are therefore beneficial in the overall ecology even though undesirable in some areas such as residential locations. Toward this end it is preferable to discourage or physically repel snakes from those areas where they are not wanted yet leave them alive to fulfill their role in the ecological scheme. Additionally, any method employed for repelling snakes should be environmentally sound and non-harmful to humans and other animals.

Accordingly, it is an object to provide a method for repelling snakes. It is a further object to provide a method for repelling snakes that is not harmful or fatal to them. It is a still further object to provide a method for repelling snakes that is simple and effective against a variety of species. It is still another object to provide a snake repellant compound that is effective, easy to use, and biologically as well as ecologically sound.

Naphthalene has been known in the past as an effective insecticide, pesticide and repellant for other creatures, particularly moles. However, its effectiveness against snakes has never been expected, much less demonstrated. Accordingly, the present inventor herein presents a new use for naphthalene in the form of a snake repellant.

DETAILED DESCRIPTION OF THE INVENTION

Snakes sense odors from the surrounding environment by "tasting" the air around them. Through the characteristic tongue flicks, quick extension and retraction of the tongue, snakes pick up odorant molecules from the air and transfer them to the vemeronasal epithelium which is a sensory tissue within the mouth. The function of this tissue is to detect, analyze, identify and locate the source of odors. A snake's responses to its environment are mediated in large part by the information obtained in this manner. Accordingly, an effective snake repellant should take into account this method of chemosensory detection and the apparent extent to which snakes rely on it.

The inventor herein has discovered that naphthalene, in combination with sulfur and montmorillonite, when compounded into a granular product of intermediate mesh provides an effective and potent snake repellant that is easily stored and applied and is non-harmful to the environment, the snakes themselves or humans and other animals.

Naphthalene is a volatile hydrocarbon having the formula $C_{10}H_8$ and the following structure:

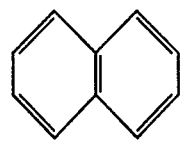

It is obtained from the middle oil fraction of coal tar oils that boil between 170° and 230° C. Following fractionation, the oils are cooled to crystallize the naphthalene which is then separated and further refined. The resulting naphthalene crystals vaporize in air to produce a strong odor that is believed to be offensive to snakes so that when it is detected, the snakes turn away from that location.

The compound of this invention comprises a mixture of naphthalene, sulfur and montmorillonite, or Fuller's Earth, ground and mixed into a dry granular form. Naphthalene is the active ingredient and is produced in the form of flakes refined to a purity of 99%. It is included in an amount of 5-10% by weight, preferably 8% by weight. Precipitated sulfur flakes are added in an amount of 30-35% by weight, preferably 32% by weight, and montmorillonite as a binder and carrier in an amount of 55-65% by weight, preferably 60% by weight. The ingredients are weighed and mixed together in any standard mixing device, although a rotary mixer is preferred, to form the granular product.

In use, the resulting granular product is spread on the ground across an area where it is desired to prevent or discourage snakes from entering. Preferably, the granules should be spread in a strip 10-30 centimeters wide, although generally the wider the strip the better. In this manner, an odor barrier is provided that snakes are reluctant to cross. Additionally, a smaller amount of the product may be scattered in a diffuse or non-continuous manner just beyond the strip, on the side away from the area to be protected. This added scattering of the repellant serves to lessen the probability of occasional snakes wandering beyond the strip.

The effectiveness of the repellant is demonstrated by the following experiments performed with various species and the product has been found to have a rate of efficacy that varies from 17% to 100% depending on the individual species with the rattlesnakes exhibiting consistently high avoidance of the product. The experiments were conducted on the following snakes:

*Agkistrodon contortrix*, copperhead
*Agkistrodon piscivorus*, water moccasin
*Coluber constrictor*, black racer
*Crotalus adamanteus*, eastern diamondback rattlesnake
*Crotalus atrox*, western diamondback rattlesnake
*Crotalus horridus*, timber rattlesnake
*Crotalus lepidus*, rock rattlesnake
*Crotalus ruber*, red diamond rattlesnake
*Crotalus viridis*, pacific rattlesnake
*Elaphe guttata*, corn or red rat snake
*Elaphe obsoleta*, yellow rat snake
*Heterodon platyrhinos*, eastern hognose snake
*Micrurus fulvius*, eastern coral snake
*Python molurus*, burmese python
*Thamnophis marcianus*, checkered garter snake In as much as the normal behavior of snakes is to move slowly in a deliberate and investigatory manner, the experiments were devised to test the snakes' responses to the repellant in as near to normal conditions as possible. Accordingly, the experiment conducted consisted of a "Y test" in which a Y shaped enclosure, approximately 3 meters long, was constructed having open arms with a 12 centimeter wide strip of the repellant applied across one of these arms at its junction with the body of the Y. The other arm was left unprotected. The snakes were released one at a time at the bottom of the Y and allowed to make their way unmolested toward the arms where they could choose the right or left-hand arm and were scored on which arm they chose.

The above noted species were tested in this manner with the following results as summarized in Table 1.

*Agkistrodon contortrix.* Eight snakes were available for testing and in the primary tests one snake crossed the repellant. One individual was re-tested three times and in each instance chose the non-repellant branch of the Y. The snake eventually crossed the repellant only when it was caused to crawl along the wall of the enclosure leading to the branch with the repellant.

*Agkistrodon piscivorus.* Nineteen snakes were available for testing, four of which exhibited rapid and frantic locomotion and were not included in the analysis. In the primary test, nine snakes chose the non-repellant branch of the Y and six snakes crossed the repellant. Two of the snakes showed overt avoidance by turning away from the repellant after investigating it, while two other snakes approached the repellant, paused, turned away momentarily, but then crossed the repellant. One of those crossing the repellant after pausing, lifted its head while doing so, effectively avoiding head contact with the chemical.

*Coluber constrictor.* Only one snake was available for testing; however, repeated tests resulted in apparent avoidance in four consecutive trials. The snake crossed the repellant during a fifth test. This snake was difficult to test because it is an active forager capable of rapid locomotion and it moved quickly in the enclosure. However, it clearly avoided the repellant during at least one of the tests.

*Crotalus adamanteus.* Thirteen snakes were available for testing but three moved rapidly and exhibited nervous, frantic behavior and were excluded from the analysis. Of the remaining ten snakes, only two crossed the repellant, four overtly avoided the repellant and a fifth individual appeared to avoid the repellant. Another snake appeared to avoid the repellant by consistently selecting the benign branch of the Y during four repetitive tests. It should be noted that this "apparent" avoidance is used to indicate consistent turning away from the repellant while at distances of 10 to 30 centimeters from it. In other words, the snakes turned away from the repellant before coming in direct contact with it.

*Crotalus atrox.* Thirteen snakes were available for testing and exhibited overt avoidance of the repellant. In every case these snakes avoided the repellant and eventually moved into the non-repellant branch of the Y. Six snakes continued to exhibit avoidance behaviors during repeat tests conducted within minutes to hours of previous exposure.

*Crotalus horridus.* Ten snakes were tested with two being excluded due to rapid movement. All of the remaining eight snakes entered the non-repellant branch of the Y in the primary tests. Three individuals were induced to cross the repellant when they were deliberately released so as to crawl along the wall of the enclosure leading to the repellant.

*Crotalus lepidus.* Five snakes of this species were available for testing. Only one individual crossed the repellant in the primary tests. Two of the remaining snakes showed overt avoidance of the repellant while the other two apparently avoided the repellant.

*Crotalus ruber.* Only one specimen of this snake was available for testing and it consistently selected the non-repellant branch of the Y during four consecutive tests and avoided the repellant well before approaching contact.

*Crotalus viridis.* Again, only one specimen was available for testing and it exhibited overt avoidance of the repellant.

*Elaphe guttata.* Twenty-six individuals were available for testing, two of which were discarded because of rapid locomotion and nervous behavior. In the primary test, fourteen snakes selected the non-repellant branch of the Y while ten crossed the repellant. Eight snakes exhibited behavioral signs of overtly avoiding contact with the repellant and four snakes crossed the repellant even though, at first contact, they exhibited avoidance behavior such as hesitation, lifting head up off the substrate, changing direction of locomotion, etc. When eight snakes were re-tested by placing them within 30 centimeters of the repellant strip and facing it, five selected the non-repellant branch of the Y and only three crossed the repellant. Two snakes exhibited avoidance behaviors and, in one case, a snake turned away from the strip and was moving in a direction that would have taken it away except that it encountered a stray pellet of the repellant, whereupon it turned again and subsequently entered the repellant branch of the Y.

*Elaphe obsoleta.* Twenty-two snakes were tested, fifteen of which were acceptable for analysis. Eleven snakes selected the non-repellant branch of the Y and four snakes crossed the repellant. Of these four, two exhibited avoidance and were diverted by the repellant momentarily, but eventually crossed the strip.

*Heterodon platyrhinos.* One snake was available for testing and exhibited overt avoidance of the repellant during consecutive tests.

*Micrurus fulvius.* Two snakes were tested and both selected the non-repellant branch of the Y. One of these avoided the repellant by turning away three different times, crawling back and then reversing. However, it eventually crawled parallel to the strip of the repellant but avoided contacting it.

*Python molurus.* Twenty snakes were tested, sixteen of which were acceptable for analysis. Of these, twelve snakes selected the non-repellant branch of the Y and three crossed the repellant. Eight snakes exhibited overt avoidance of the repellant, and others appeared to avoid the repellant by consistently turning away from it before contact. Two of the snakes which crossed the repellant vibrated their tales while doing so.

*Thamnophis marcianus.* Twenty-five snakes were tested and exhibited 100% avoidance of the repellant during primary tests. Eighteen of these snakes exhibited overt avoidance of the repellant with typical behavior involving jerking the head away from the repellant after approaching it with tongue flicks, then crawled away, often rubbing the sides of the head along the ground for a brief period. Upon re-testing, one snake began rubbing its head on the ground, crawling haphazardly, and eventually tunneled its way through the repellant strip.

The foregoing results are summarized in the following table.

TABLE 1

Choices of snakes tested in Y enclosure. All data are for primary tests, and the numbers of snakes repelled are calculated as desribed above.

| Species | Snakes Crossing Repellant/Snakes Repelled | % Repelled |
| --- | --- | --- |
| Agkistrodon contortrix | 1/8 | 86 |
| Agkistrodon piscivorus | 6/15 | 21 |
| Crotalus (all species) | 2/37 | 91 |
| Elaphe guttata | 10/24 | 17 |
| Elaphe obsoleta | 4/15 | 47 |
| Python molurus | 3/15 | 50 |
| Thamnophis marcianus | 0/25 | 100 |
| All Other Species | 0/4 | 100 |

As the Table shows, of 143 valid tests only 26 snakes actually crossed the repellant and many of those exhibited some avoidance behavior even when crossing the strip. Snakes that exhibited rapid or frantic locomotion were excluded from the test results as such behavior reflects an intention to escape and is not accompanied by the constant, frequent tongue flicks by which snakes obtain their chemosensory information. Accordingly, these tests ably demonstrate that the present invention is an effective snake repellant for a variety of species, particularly venomous types such as copperheads and rattlesnakes.

What is claimed is:

1. A method of repelling snakes comprising spreading a granular composition containing a volatile active ingredient in a strip on the ground about an area to be protected wherein the active ingredient is allowed to vaporize, producing an odor that is offensive to snakes but not physically harmful to them; said granular compound comprising naphthalene, sulfur and montmorillonite.

2. The method of claim 1 wherein the composition is spread in a strip from 10–30 centimeters wide.

3. The method of claim 2 further comprising scattering a smaller amount of the composition beyond the strip on the side away from the area to be protected.

4. The method of claim 1 employing a composition comprising 8% by weight of naphthalene, 32% by weight of sulfur and 60% by weight of montmorillonite.

5. The method of claim 1, wherein the naphthalene has a purity of 99% and is included in an amount of 5–10% by weight.

6. The method of claim 5 wherein the sulfur is in the form of precipitated flakes and is included in an amount of 30–35% by weight.

7. The method of claim 6 wherein the montmorillonite is included in an amount of 55–65% by weight.

8. The method of claim 1 comprising spreading a composition comprising 5–10% by weight of naphthalene, 30–35% by weight of sulfur and 55–65% by weight of a binder mixed together to form a granular product.

* * * * *